United States Patent [19]

Cook, Jr.

[11] 4,034,064
[45] July 5, 1977

[54] HYDROGEN PEROXIDE STABILIZATION WITH TRIAMIDES OF PHOSPHORUS

[75] Inventor: James A. Cook, Jr., Barberton, Ohio

[73] Assignee: PPG Industries, Inc., Pittsburgh, Pa.

[22] Filed: Feb. 2, 1976

[21] Appl. No.: 654,312

[52] U.S. Cl. .............................. 423/272; 423/584
[51] Int. Cl.$^2$ .............................................. C01B 15/02
[58] Field of Search .................. 423/272, 273, 584; 252/186; 260/551 P

[56] References Cited

UNITED STATES PATENTS

| | | | |
|---|---|---|---|
| 825,883 | 7/1905 | Heinrici | 423/272 |
| 2,871,101 | 1/1959 | Rust et al. | 423/272 |
| 3,122,417 | 2/1964 | Blaser et al. | 423/272 |
| 3,781,409 | 12/1973 | Munday et al. | 423/273 |
| 3,860,391 | 1/1975 | Kling et al. | 252/186 |
| 3,903,244 | 9/1975 | Winkley | 423/272 |

FOREIGN PATENTS OR APPLICATIONS

| | | | |
|---|---|---|---|
| 791,614 | 8/1968 | Canada | 423/584 |

Primary Examiner—O. R. Vertiz
Assistant Examiner—Wayne A. Langel
Attorney, Agent, or Firm—William M. Dooley

[57] ABSTRACT

Aqueous hydrogen peroxide solutions are stabilized with the use of phosphorous triamides and phosphoric triamides such as hexamethylphosphorous triamide, hexamethylphosphoric triamide, and bis(dimethylamino)morpholinophosphorus oxide, preferably in combination with known stabilizer additives, i.e., stannates, nitrates, and pyrophosphates.

12 Claims, No Drawings

HYDROGEN PEROXIDE STABILIZATION WITH TRIAMIDES OF PHOSPHORUS

BACKGROUND OF THE INVENTION

This invention relates to retarding the decomposition of hydrogen peroxide in aqueous solution.

Dilute aqueous hydrogen peroxide in concentrations of between about 3 and 10 weight percent has many uses, including bleaching, hair dyeing and waving, processing of photographs for permanence, and preparation of cosmetics and mild antiseptics.

Hydrogen peroxide is commonly sold in concentrated aqueous solutions of between about 30 and 90 weight percent, which are often diluted by the purchaser for use or sale. The concentrated solutions are quite stable when pure, but contaminants which promote decomposition may be introduced in storage and handling. The common use of tap water for dilution of the concentrate may introduce significant quantities of decomposition-inducing cations such as iron, copper, and manganese cations. If diluted solutions are stored rather than used immediately, substantial decomposition may occur.

Numerous organic and inorganic stabilizers for aqueous hydrogen peroxide are known. Various combinations of stannate, nitrate, orthophosphate, and pyrophosphate ions for use at varying pH have been proposed. See, for example, U.S. Pat. Nos. 3,701,825, 3,373,113, 3,591,341, and 3,607,053. U.S. Pat. No. 3,781,409 discloses the use of water-soluble tin compounds, preferably in conjunction with organic complexing agents such as organic phosphonic acids, 8-hydroxyquinoline, hydroquinone, nitrilo triacetic acid, alkyl phenols, and phosphate esters.

U.S. Pat. Nos. 3,453,231, 3,472,814, 3,420,792, and 3,429,850 disclose the use of hexaalkylphosphoric triamides to stabilize polyphenylene ethers. U.S. Pat. No. 3,376,232 discloses the use of the hexaalkylphosphorus and hexaalkylphosphoric triamides to stabilize antioxidant and antiozonant stanbilizers for organic substances.

It has now been found that decomposition of aqueous hydrogen peroxide solutions may be retarded by dissolving therein a minor stabilizing concentration of certain triamides of phosphorus.

The triamide may be used alone or, preferably, in combination with known stabilizing additives, notably stannates. More preferably, the triamide is used in combination with stannates, nitrates, and pyrophosphates.

DETAILED DESCRIPTION OF THE INVENTION

In accordance with this invention, a stabilized aqueous hydrogen peroxide solution is prepared having dissolved therein a minor stabilizing amount of a soluble triamide of phosphorus.

Useful soluble triamides of phosphorus may be represented by the formulas:

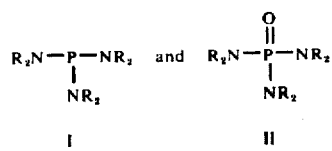

wherein (a) each R independently is a lower alkyl group having from 1 to 6, preferably 1 to 3, carbons such as methyl, ethyl, isopropyl, secbutyl, and n-hexyl, (b) the two R on a particular nitrogen may be joined, optionally through an oxygen atom, to form together with the nitrogen atom a ring such as a piperidine or a morpholine ring, and (c) the total number of carbons in all R is from 6 to 20 inclusive. Compounds of formula I are phosphorous triamides; compounds of formula II are phosphoric triamides. It is contemplated that when phosphorous triamides have been dissolved in aqueous hydrogen peroxide, they may be oxidized to a greater or lesser extent to the corresponding phosphoric triamide. Mixtures of triamides of phosphorus may also be used.

It is estimated that above-described triamides of phosphorus having a total of up to 20 carbons will be sufficiently soluble in aqueous hydrogen peroxide solutions to retard decomposition. Triamides having from 6 to 12 carbons will be more readily soluble and are therefore preferred. Triamides having oxygen-containing rings, such as bis(dimethylamino)morpholinophosphorus oxide, are also readily soluble.

Hexamethylphosphorous triamide, hexamethylphosphoric triamide, and bis(dimethylamino)morpholinophosphorus oxide have been found effective in retarding the decomposition of aqueous hydrogen peroxide and are preferred for their solubility. Other hexaalkyl triamides of phosphorus which are expected to have a beneficial stabilizing effect include, for example, hexaethylphosphoric triamide, bis(diethylamino)piperidinophosphorus oxide, hexa-n-propylphosphoric triamide, N-methyl-N-n-butyl-N',N''-tetramethylphosphoric triamide, N,N', N''-trimethyl-N,N',N''-tri-n-butylphosphoric triamide, N-diisopropyl-N',N''-tetramethylphosphoric triamide, and N-methyl-N-ethyl-N',N''-tetraethylphosphorous triamide.

It has been reported that hexamethylphosphoramide induced cancer in rats which breathed the vapor for 6 to 8 months. Chemical & Engineering News, Vol. 53, No. 39, p. 17 (Sept. 29, 1975). This report must be taken into consideration when aqueous hydrogen peroxide intended for food, drug, or cosmetic use is prepared.

A method useful for the preparation of the named triamides of phosphorus and others is disclosed in U.S. Pat. No. 3,531,550, particularly columns 6 and 7 and Examples 40–45, wherein an appropriate secondary amine such as dimethylamine or morpholine is reacted with a phosphorus compound such as phosphorus trichloride, phosphorus oxychloride, N-di-n-propylphosphoroamide dichloride, or bis(dimethylamino)phosphorochloridate to form a corresponding phosphorous or phosphoric triamide. Phosphorous triamides may also be ozone oxidized to form phosphoric triamides.

The stabilizing triamides of phosphorus herein contemplated may be included in widely varying concentrations in aqueous hydrogen peroxide solutions of any substantial concentration to retard the decomposition of the hydrogen peroxide, particularly to retard decomposition induced by polyvalent metal cation contaminants. The preferred stabilizer concentration depends upon the amount of contamination anticipated. Where a hydrogen peroxide solution is to be stabilized, for example, against contaminant cations introduced in handling or by dilution with tap water, a useful stabilizing concentration of triamide of phosphorus usually will be from about 0.01 to about 2.0 weight percent, more preferably from about 0.05 to about 0.5 weight percent, by weight of hydrogen peroxide. Amounts of more than about 2.0 weight percent may be used, but do not appear to have advantage over lower amounts, and excessive amounts of stabilizer may be less effective than preferred amounts.

Stabilized hydrogen peroxide solutions of any substantial hydrogen peroxide concentration may be prepared. Thus, aqueous hydrogen peroxide solutions of between about 3 and 90 weight percent hydrogen peroxide may be stabilized in accordance with this invention. Especially useful are about 30 to 70 weight percent solutions, which may be shipped conveniently and then diluted by the user to a desired concentration, typically about 3 to 10 weight percent.

The stabilized solutions are kept acidic, having a pH usually between about 1 and 6, preferably between about 1 and 4.5, as measured with a glass electrode, depending upon the concentration of hydrogen peroxide. If the stabilized solution is dilute, i.e., between about 3 and 10 weight percent, especially if the dilute solution is to be stored for a time, it is desirable to adjust the pH to between about 3 and 4.5. More concentrated solutions usually have a lower pH. For example, a 30 weight percent solution will usually have a pH of about 2.5 to 3. A 70 weight percent solution may have a pH of 1 or even lower. The pH of a stabilized solution may be lowered by the addition of orthophosphoric acid, nitric acid, or another organic or inorganic acid inert to hydrogen peroxide. The pH may be raised by the addition of sodium hydroxide, sodium carbonate, trisodium phosphate, or another alkaline material inert to hydrogen peroxide.

It is highly preferred to use the stabilizers of this invention in combination with stannate compounds in stabilized aqueous hydrogen peroxide. More preferably, the stabilizers are used in combination with stannates, nitrates, and inorganic phosphates.

Useful stannate compounds include ammonium and alkali metal stannates such as sodium stannate, potassium stannate, and ammonium stannate. Sodium stannate trihydrate is preferred. The stannate compound may be used in an amount of between about 0.001 and 1.0 weight percent or more (calculated as sodium stannate trihydrate), usually between about 0.01 and 0.5 weight percent by weight of hydrogen peroxide. When a stannate compound is used, it should be added to the hydrogen peroxide solution before other additives in order to avoid difficulty in dissolving the stannate.

The presence of nitrate ion in aqueous hydrogen peroxide solution inhibits corrosion of the aluminum vessels in which the solutions are manufactured and stored. Sources of nitrate ion include nitric acid, alkali metal nitrates such as sodium nitrate, and ammonium nitrate. The amount of nitrate used may be between about 0.001 and 1.0 weight percent or more (calculated as ammonium nitrate), usually between about 0.01 and 0.5 weight percent, by weight of hydrogen peroxide.

Inorganic phosphate, i.e., orthophosphate or, preferably, pyrophosphate, may also be included to further increase the stability of hydrogen peroxide solutions stabilized according to this invention. Sources of inorganic phosphate include orthophosphoric acid, pyrophosphoric acid, and their alkali metal and ammonium salts, such as disodium hydrogen phosphate, disodium dihydrogen pyrophosphate, tetrasodium pyrophosphate, and ammonium dihydrogen phosphate. The inorganic phosphate may be used in amounts of between about 0.001 and 2.0 weight percent or more (calculated as disodium dihydrogen pyrophosphate), preferably between about 0.005 and 0.75 weight percent by weight of hydrogen peroxide. Pyrophosphate is preferred.

Especially desirable stabilized aqueous hydrogen peroxide solutions have dissolved therein between about 0.25 and 0.35 weight percent of stabilizing triamide of phosphorus, between about 0.05 and 0.08 weight percent nitrate calculated as ammonium nitrate, between about 0.12 and 0.16 weight percent stannate calculated as sodium stannate trihydrate, and between about 0.10 and 0.18 weight percent pyrophosphate calculated as disodium dihydrogen pyrophosphate, at a pH of between about 3.0 and 1.0, and hydrogen peroxide concentrations of between about 30 and 70 weight percent. The additive concentrations are by weight of hydrogen peroxide.

The stabilizer compounds of this invention may be added directly to the aqueous hydrogen peroxide to be stabilized, or they may first be dissolved in water or aqueous hydrogen peroxide either alone or together with other additives. However, an additive solution containing both a triamide of phosphorus and a stannate should not be allowed to stand for a long time before being added to the aqueous hydrogen peroxide to be stabilized, or lower stability may result.

The following examples illustrate how the present invention may be practiced. In the examples, stabilized hydrogen peroxide solutions of about 35 weight percent concentration were prepared, portions were diluted to about 6 weight percent, and portions of the 6 percent solutions were treated with a contaminant cation solution containing either 2 or 5 cations. Then portions of the contaminated 6 percent solutions were tested for stability.

The two cation contaminant solution was prepared from aqueous $Fe(NO_3)_3 \cdot 9H_2O$ and $Cu(NO_3)_2 \cdot 3H_2O$. In each case when it was used, sufficient of this solution was added to the 6 weight percent hydrogen peroxide test solution to provide the following concentrations of ions in each such test solution:

| | | |
|---|---|---|
| $Fe^{+++}$ | 2.5 | milligrams/liter |
| $Cu^{++}$ | 0.075 | milligrams/liter |

The five cation contaminant solution was prepared from aqueous solutions of $AlK(SO_4)_2 \cdot 12H_2O$, $FeNH_4(SO_4)_2$, $CuSO_4$, $MnSO_4$, and $K_2CrO_4$. In each case when it was used, sufficient of this solution was added to the 6 weight percent hydrogen peroxide test solution to provide the following concentrations of ions in each such test solution:

| | | |
|---|---|---|
| $Al^{+++}$ | 0.25 | milligrams/liter |
| $Fe^{+++}$ | 0.25 | milligrams/liter |
| $Cu^{++}$ | 0.05 | milligrams/liter |
| $Mn^{++}$ | 0.025 | milligrams/liter |
| $Cr^{++++++}$ | 0.012 | milligrams/liter |

Stability of tested solutions was measured by the $S_{100}$ test. This test is performed by placing a weighed sample of test solution, about 45 milliliters, in a 50 milliliter volumetric-type flask having an extra-long neck. (The flask is passivated overnight with 35 percent nitric acid before use.) The body of the flask is then immersed up to the neck in water at 100° C. for 24 hours, with the mouth of the flask lightly covered but not sealed. The flask neck, which extends above the heat bath, serves as a condenser to minimize loss of water from the test solution. After 24 hours, the weight of test solution remaining in the flask is determined and expressed as a percentage of the initial weight. This percentage is the $S_{100}$ value. A high $S_{100}$ value corresponds to a low loss of oxygen from the solution and therefore to high stability of the hydrogen peroxide.

EXAMPLE I

Hexamethylphosphoric Triamide

Hexamethylphosphoric triamide was incorporated as a stabilizer in aqueous hydrogen peroxide solutions of about 35 weight percent (30 percent in Experiment 1) containing various concentrations of sodium stannate trihydrate, ammonium nitrate, and disodium dihydrogen pyrophosphate. Portions of these solutions were then diluted to about 6 weight percent hydrogen peroxide. The pH of the diluted solutions was adjusted to the values shown in Table I by the addition of dilute nitric acid or sodium hydroxide as required, and each test solution was treated with either the 2 or the 5 cation contaminant solution as indicated in the Table. The contaminated solutions were then tested for stability by the $S_{100}$ test.

In Table I, the stannate, nitrate, and pyrophosphate concentrations in the initial 35 (or 30) weight percent solution are listed as percent by weight of hydrogen peroxide. In Experiment 1, the concentration of hexamethylphosphoric triamide in the 30 percent solution was 0.33 weight percent; in Experiments 2 through 11, it was 0.28 weight percent by weight of hydrogen peroxide. The remainder of the Table lists the pH, actual assay, and $S_{100}$ of the 6 percent test solutions and indicates which contaminant cation solution (2 or 5) was used in the test solutions.

TABLE I

| HYDROGEN PEROXIDE SOLUTIONS STABILIZED WITH HEXAMETHYLPHOSPHORIC TRIAMIDE, 0.28%[1] | | | | | | | |
|---|---|---|---|---|---|---|---|
| Experiment | Stannate, %[2] | Nitrate, %[3] | Pyrophosphate, %[4] | pH | Assay, %[5] | Contaminated Cations | $S_{100}$, % |
| 1 | 0.16 | 0.033 | — | 3.6 | 5.93 | 2[5] | 90.2 |
| 2 | 0.14 | 0.064 | — | 3.5 | 5.75 | 2 | 88.6 |
| 3 | 0.14 | 0.064 | — | 3.5 | 5.93 | 5[6] | 84.1 |
| 4 | 0.07 | 0.064 | — | 4.5 | 5.82 | 5 | 80.3 |
| 5 | 0.07 | 0.064 | — | 3.5 | 5.73 | 5 | 72.4 |
| 6 | 0.14 | 0.064 | — | 4.5 | 5.97 | 5 | 85.4 |
| 7 | 0.14 | 0.064 | — | 3.5 | 5.92 | 5 | 92.6 |
| 8 | 0.21 | 0.064 | — | 4.5 | 5.93 | 5 | 88.7 |
| 9 | 0.21 | 0.064 | — | 3.5 | 5.89 | 5 | 92.1 |
| 10 | 0.14 | 0.064 | — | 3.5 | 6.03 | 5 | 77.0 |
| 11 | 0.14 | 0.064 | 0.14 | 3.5 | 6.11 | 5 | 95.3 |

[1]0.33% in Experiment 1
[2]As sodium stannate trihydrate, by weight of hydrogen peroxide
[3]As ammonium nitrate
[4]As disodium dihydrogen pyrophosphate
[5]Fe$^{+++}$ (2.5 mg/l) and Cu$^{++}$ (0.075 mg/l)
[6]Al$^{+++}$ (0.25 mg/l), Fe$^{+++}$ (0.25 mg/l), Cu$^{++}$ (0.05 mg/l), Mn$^{++}$ (0.025 mg/l), and Cr$^{++++++}$ (0.012 mg/l).

The results in Table I demonstrate that hexamethylphosphoric triamide is effective in stabilizing aqueous hydrogen peroxide against cation-induced decomposition. Experiments 3 through 9 show the effects of changes in stannate concentration and pH. Experiments 10 and 11 show that the presence of pyrophosphate even further improves the stability of aqueous hydrogen peroxide containing hexamethylphosphoric triamide, stannate, and nitrate.

EXAMPLE II

Hexamethylphosphorous Triamide
Bis(dimethylamino)morpholinophosphorus Oxide A series of aqueous hydrogen peroxide solutions were prepared using hexamethylphosphorous triamide or bis(dimethylamino)morpholinophosphorus oxide as the stabilizer, in each case at 0.28 weight percent, in the manner described in Example I. Shortly after preparation, slight flocculent precipitates formed in the 35 percent solutions containing the hexamethylphosphorous triamide. An incendiary reaction occurred when 35 percent peroxide was poured onto hexamethylphosphorous triamide. Other methods of incorporation, such as adding the triamide to the peroxide, are recommended. The results of these experiments are reported in Table II.

TABLE II

| HYDROGEN PEROXIDE SOLUTIONS STABILIZED WITH HEXAMETHYLPHOSPHOROUS TRIAMIDE[1] OR BIS(DIMETHYLAMINO)MORPHOLINOPHOSPHORUS OXIDE[2] | | | | | | | |
|---|---|---|---|---|---|---|---|
| Experiment | Stannate, % | Nitrate, % | Pyrophosphate, % | pH | Assay, % | Contaminant Cations | $S_{100}$, % |
| 12 | 0.14 | 0.064 | — | 3.5 | 5.82 | 2 | 93.3 |
| 13 | 0.14 | 0.064 | — | 3.5 | 5.59 | 2 | 88.8 |
| 14 | 0.14 | 0.064 | — | 3.5 | 5.70 | 5 | 90.8 |
| 15 | 0.21 | 0.064 | — | 3.5 | 5.71 | 2 | 96.2 |
| 16 | 0.21 | 0.064 | — | 3.5 | 5.82 | 5 | 96.0 |
| 17 | 0.28 | 0.064 | — | 3.5 | 5.76 | 2 | 99.5 |
| 18 | 0.28 | 0.064 | — | 3.5 | 5.79 | 5 | 87.9 |
| 19 | 0.07 | 0.064 | — | 4.5 | 5.90 | 5 | 74.8 |
| 20 | 0.07 | 0.064 | — | 3.5 | 5.76 | 5 | 65.8 |
| 21 | 0.14 | 0.064 | — | 4.5 | 5.84 | 5 | 93.5 |
| 22 | 0.14 | 0.064 | — | 3.5 | 5.83 | 5 | 95.1 |
| 23 | 0.21 | 0.064 | — | 4.5 | 5.81 | 5 | 92.6 |
| 24 | 0.21 | 0.064 | — | 3.5 | 5.90 | 5 | 95.1 |

TABLE II-continued
HYDROGEN PEROXIDE SOLUTIONS STABILIZED WITH HEXAMETHYLPHOSPHOROUS TRIAMIDE[1] OR BIS(DIMETHYLAMINO)MORPHOLINOPHOSPHORUS OXIDE[2]

| Experiment | Stannate, % | Nitrate, % | Pyrophosphate, % | pH | Assay, % | Contaminant Cations | $^s$100, % |
|---|---|---|---|---|---|---|---|
| 25 | 0.14 | 0.064 | — | 3.5 | 5.96 | 5 | 89.2 |
| 26 | 0.14 | 0.064 | 0.14 | 3.5 | 6.02 | 5 | 89.4 |

[1]Experiments 12-24
[2]Experiments 25-26

The results in Table II demonstrate that hexamethylphosphorous triamide is effective in stabilizing aqueous hydrogen peroxide against cation-induced contamination. Experiments 12 through 18 show the use of varying stannate levels and two different contaminant ion solutions. Experiments 19 through 24 show the use of varying stannate levels and pH.

Experiments 25 and 26 show that bis(dimethylamino)morpholinophosphorus oxide is also effective.

EXAMPLE III
Reference Formulations Containing Stannate, Nitrate, and Pyrophosphate For comparison, Table III summarizes the results obtained with solutions prepared as described in Example I, but containing only sodium stannate trihydrate, ammonium nitrate, and disodium dihydrogen pyrophosphate as stabilizers.

In Experiments 27 and 28, the test solutions were prepared from stabilized 30 weight percent hydrogen peroxide solutions. The remainder were prepared from stabilized 35 percent solutions.

TABLE III
HYDROGEN PEROXIDE SOLUTIONS STABLIZED WITH STANNATE, NITRATE, AND PYROPHOSPHATE

| Experiment | Stannate, % | Nitrate, % | Pyrophosphate, % | pH | Assay, % | Contaminant Cations | $^s$100, % |
|---|---|---|---|---|---|---|---|
| 27 | 0.16 | 0.033 | 0.32 | 3.6 | 5.96 | 2 | 85.0 |
| 28 | 0.16 | 0.033 | — | 3.6 | 6.00 | 2 | 88.2 |
| 29 | 0.14 | 0.028 | 0.14 | 3.5 | 5.57 | 2 | 19.7 |
| 30 | 0.14 | 0.064 | 0.28 | 3.5 | 5.82 | 2 | 57.6 |
| 31 | 0.14 | 0.064 | 0.28 | 3.5 | 5.89 | 2 | 56.5 |
| 32 | 0.14 | 0.064 | 0.28 | 3.5 | 5.88 | 5 | 82.7 |
| 33 | 0.14 | 0.064 | 0.28 | 3.5 | 5.92 | 5 | 75.2 |
| 34 | 0.14 | 0.064 | 0.28 | 3.5 | 5.99 | 5 | 30.0 |

The results in Table III show stabilities attained with the use of conventional stannate, nitrate, and pyrophosphate stabilizers. The reason for the variations in result are not understood, but it is apparent that these solutions are generally less stable than those reported in Tables I and II.

EXAMPLE IV
Aluminum Corrosion Test

A 35 weight percent aqueous hydrogen peroxide solution was prepared containing 0.28 weight percent hexamethylphosphoric triamide, 0.14 weight percent sodium stannate trihydrate, and 0.064 weight percent ammonium nitrate. Two passivated glass jars were charged with 100 milliliter portions of the peroxide solution. Into one jar was placed a 4 by 1 by ⅛ inch piece of aluminum cut from a 1060 aluminum pipe, and having a bead of 1260 aluminum welded thereon. The piece was partially immersed in the peroxide solution up to the weld bead. The bottles were covered with Saran film, capped loosely, and stored at 40° C. for 5 weeks and 45° C. for 6 weeks. At the end of the 11$^{th}$ week, a slight amount of fine white flocculent precipitate was observed in the bottle containing the aluminum. The portion of the aluminum which had been above the peroxide solution was unchanged; the portion below was stained, but no pitting or corrosion was noted.

Although this invention has been described with reference to particular details, experiments, and preferred embodiments, the particulars of the description are not intended to limit the scope of the invention except insofar as they appear in the following claims.

I claim:

1. A stabilized aqueous hydrogen peroxide solution having dissolved therein a minor stabilizing concentration, sufficient to retard decomposition of hydrogen peroxide induced by polyvalent metal cation contamination, of a phosphorus compound selected from the group consisting of compounds represented by the formula:

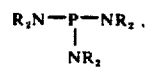

compounds represented by the formula

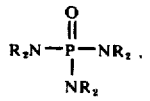

and mixtures thereof, wherein (a) each R independently is an alkyl group having 1 to 6 carbons, (b) the two R on a particular nitrogen may be joined, optionally through an oxygen, to form a ring together with the nitrogen, and (c) the total number of carbons in all R is from 6 to 20.

2. The hydrogen peroxide solution of claim 1 having dissolved therein between about 0.01 and 2.0 weight percent, by weight of hydrogen peroxide, of the phosphorus compound, between about 0.001 and 1.0 weight percent, calculated as sodium stannate trihydrate, of an alkali metal or ammonium stannate and between about 0.001 and 1.0 weight percent, calculated as ammonium nitrate, of nitric acid or an alkali metal or ammonium nitrate.

3. The hydrogen peroxide solution of claim 2 further having dissolved therein between about 0.001 and 2.0 weight percent, calculated as disodium dihydrogen pyrophosphate, of pyrophosphoric acid or an alkali metal or ammonium pyrophosphate.

4. The hydrogen peroxide solution of claim 1, wherein the phosphorus compound is hexamethylphosphoric triamide.

5. The hydrogen peroxide solution of claim 1, wherein the phosphorus compound is hexamethylphosphorous triamide.

6. The hydrogen peroxide solution of claim 1, wherein the phosphorus compound is bis(dimethylamino)morpholinophosphorus oxide.

7. A method of stabilizing aqueous hydrogen peroxide, which comprises:
adding to aqueous hydrogen peroxide solution a minor stabilizing amount, sufficient to retard decomposition of hydrogen peroxide induced by polyvalent metal cation contamination, of a soluble phosphorus compound selected from the group consisting of compounds represented by the formula:

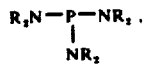

compounds represented by the formula

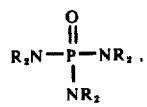

and mixtures thereof, wherein (a) each R independently is an alkyl group having 1 to 6 carbons, (b) the two R on a particular nitrogen may be joined, optionally through an oxygen, to form a ring together with the nitrogen, and (c) the total number of carbons in all R is from 6 to 20.

8. The method of claim 7 which further comprises adding between about 0.01 and 2.0 weight percent, by weight of hydrogen peroxide, of the soluble phosphorus compound, between about 0.001 and 1.0 weight percent, calculated as sodium stannate trihydrate, of an alkali metal or ammonium stannate and between about 0.001 and 1.0 weight percent, calculated as ammonium nitrate, of nitric acid or an alkali metal or ammonium nitrate.

9. The method of claim 8 which further comprises adding between about 0.001 and 2.0 weight percent, calculated as disodium dihydrogen pyrophosphate, of pyrophosphoric acid or an alkali metal or ammonium pyrophosphate.

10. The method of claim 7, wherein the soluble phosphorus compound is hexamethylphosphoric triamide.

11. The method of claim 7, wherein the soluble phosphorus compound is hexamethylphosphorous triamide.

12. The method of claim 7, wherein the soluble phosphorus compound is bis(dimethylamino)morpholinophosphorus oxide.

* * * * *